United States Patent
Dave

(10) Patent No.: US 7,537,005 B2
(45) Date of Patent: May 26, 2009

(54) DOSE DISPENSING SYSTEM AND APPARATUS

(75) Inventor: Rajiv Bobby Dave, Edgware (GB)

(73) Assignee: GW Pharma Limited, Salisbury (GB)

( * ) Notice: Subject to any disclaimer, the term of this patent is extended or adjusted under 35 U.S.C. 154(b) by 695 days.

(21) Appl. No.: 10/505,540

(22) PCT Filed: Feb. 24, 2003

(86) PCT No.: PCT/GB03/00766

§ 371 (c)(1),
(2), (4) Date: Aug. 23, 2004

(87) PCT Pub. No.: WO03/070304

PCT Pub. Date: Aug. 28, 2003

(65) Prior Publication Data

US 2005/0150488 A1    Jul. 14, 2005

(30) Foreign Application Priority Data

Feb. 22, 2002 (GB) ................................. 0204208.3
Feb. 22, 2002 (GB) ................................. 0204210.9
Feb. 22, 2002 (GB) ................................. 0204211.7

(51) Int. Cl.
*A61M 11/00* (2006.01)

(52) U.S. Cl. ............................ 128/200.14; 128/200.23; 128/204.23

(58) Field of Classification Search ............ 128/202.22, 128/200.14, 200.23, 204.21, 204.23, 205.23; 600/300

See application file for complete search history.

(56) References Cited

U.S. PATENT DOCUMENTS

| 5,267,174 A | 11/1993 | Kaufman et al. |
| 5,408,443 A | 4/1995 | Weinberger |
| 5,694,919 A | 12/1997 | Rubsamen et al. |
| 5,720,770 A * | 2/1998 | Nappholz et al. ............. 607/30 |
| 6,032,155 A | 2/2000 | de la Huerga |
| 6,579,231 B1 * | 6/2003 | Phipps ....................... 600/300 |

FOREIGN PATENT DOCUMENTS

| EP | 1291802 A2 | 3/2003 |
| GB | 2368061 A | 4/2002 |
| WO | WO 94/16755 A | 8/1994 |
| WO | WO 01/93801 A1 | 12/2001 |
| WO | WO 02/05879 A1 | 1/2002 |
| WO | WO 03/043684 A1 | 5/2003 |

* cited by examiner

*Primary Examiner*—Steven O Douglas
(74) *Attorney, Agent, or Firm*—Wolf, Greenfield & Sacks, P.C.

(57) ABSTRACT

A dispensing system for medication comprising a dispenser (55, 56) into which the canister (60) of medication is placed. The dispenser has a locking mechanism for selectively preventing dispensing of the medication. The system receives input data from a user and has a control device remote from the dispenser to lock the dispenser until the input data is correctly entered. The dispenser may be configured by a cartridge (100) inserted into the dispenser in place of the canister (60). The dispenser also has means for determining its location and locking the device if the dispenser is not at or within a fixed location.

11 Claims, 7 Drawing Sheets

DOSE DISPENSING SYSTEM AND APPARATUS

RELATED APPLICATIONS

This application is a national stage filing under 35 U.S.C. § 371 of PCT International application PCT/GB03/00766, filed Feb. 24, 2003, which was published under PCT Article 21(2) in English, which claims priority to Great Britain patent applications GB 0204208.3, filed Feb. 22, 2002, GB 0204210.9, filed Feb. 22, 2002 and GB 0204211.7, filed Feb. 22, 2002 the entire contents of which applications are incorporated by reference herein.

RELATED ART

This invention relates to a dose dispensing system and apparatus, particularly though not exclusively for dispensing doses of drugs and other like medicaments. It can, however, be used in analogous areas where controlled dispensing of materials is desired. It is of particular value for dispensing measured doses of fluent medication from a storage container containing a reservoir of such medication, although it can also be used to dispense unit dosages of solids such as, for example, tablets.

Pharmaceutical packaging is normally designed to make access by the patient easy and unrestricted. There are, however, situations where considerations of safety and security make it necessary to control and record the usage of medicines by patients. Additionally, supervision of dosage by medical, nursing and care staff is time-consuming and costly, particularly if the patient is not in a hospital or other care facility. This is especially the case if the patient needs to take a combination of medicines with a strict regime of medication. Also, while in the case of many medicaments and pharmaceuticals the dosage regime may be subject to wide variation without potential danger to the patient on the one hand or loss of effectiveness of the medication on the other, it is well understood that medication is desirably effected using a regular dosage regime. It is found that this is not always easiest achieved simply by relying on a patient to follow written instructions. Attempts have accordingly been made to develop devices which are themselves essentially "programmed" to dispense medicament at the correct intervals, but such systems have tended to be of narrow applicability and complex and, indeed, to be easily defeated. Thus, suggestions have been made in the case of multiple pill-based medication regimes, to provide automated dispensing devices. U.S. Pat. Nos. 5,752,621 and 5,472,113 both disclose apparatus which can be used to dispense, at appropriate times, various pills in appropriate combinations. Further prior art dispensing apparatus is referred to in each of these specifications.

Devices for dispensing fluent materials such as drugs and medicaments are known in a wide variety of forms. Generally they consist of a container which is sealed and from which a suitable dose of material may be ejected. One particular widespread presentation for drugs, particularly the treatment of asthma, is that of a small pressurised canister having a valve at one end and a dispensing tube fitted with a nozzle. So-called inhalers are well-known and widely used by asthmatics. In principle, however, such a presentation is not in any sense restricted to drugs for use in treating asthma, but can be used for a wide variety of medicaments and pharmaceuticals. The mode of administration additionally does not always have to be by way of an aerosol spray. For example, it is entirely conceivable to dispense pasty or creamy formulations from a canister with some form of pump valve on it. Even discrete dosage forms such as pills may be presented in container from which pills may be released one at a time. This is a particularly preferred dosage approach presentation for homeopathic remedies where it is believed highly desirable that the pill may be taken without being handled by the person taking it more than strictly necessary. Alternatively, pills may be incorporated into a strip or ribbon which may be fed out from a cassette or the like one by one, and released from the strip for administration.

A separate consideration in connection with the administration of medicaments arises in the case of controlled clinical trials, or even, though to a lesser extent, patient monitoring. It is particularly important in a controlled clinical trial to ensure not only that the dosage regime is followed, but that a positive record is secured which enables that to be verified. Any such system should, of course, not be capable of being falsified by the patient.

A further separate consideration which applies in some cases is the strong desirability of avoiding overdosing. This can be of particular importance in the case of medicaments used in diabetes treatment where they can have extremely adverse effects if not used in the right quantity at the right time.

Yet a further problem which arises in connection with the controlled administration of medicaments in unsupervised conditions is to ensure that the right medicament is being administered, and in the case of controlled or prescription medicines, that no diversion occurs.

We have now found that substantial advantages may be obtained, but in cost-effective fashion, by providing improved dispensing systems which enable a dose of medicament or the like to be dispensed from a sealed or sealable container in accordance with a programmed regime and which are so arranged that the regime must essentially be adhered to.

Our earlier WO 02/32487 discloses a dispensing system consisting of a programmable dispensing mechanism adapted to receive a sealed or resealable container containing multiple doses of material to be dispensed, and including a mechanical actuation mechanism which, when actuated, causes a measured dose of material to be dispensed from the material container, and wherein the mechanism may be inhibited from operation by a locking mechanism which, when actuated, locks the device against the further dispensing of a dose of material until released in accordance with a desired dispensing programme, and wherein the container and dispensing mechanism are provided with means enabling the authenticity of the container placed in the dispensing mechanism to be checked.

Such release may be effected, for example, merely by the passage of sufficient time or, and this is generally preferred, by means of the release of a suitable latching mechanism which acts to lock the device against dispensing until such release is effective. The latching mechanism may be mechanical, electrical or electromechanical, but, in every case, must be as a whole programmable with the desired dosage regime. The release may be effected by suitable actuation locally or by remote control.

Preferably the container has an identification tag associated therewith and containing information about its content, and the dispensing mechanism includes means for addressing the tag and validating the dosage regime in accordance with a preset programme. The tag may take the form of a simple marking on the face of the container such as a barcode, or it may be a more sophisticated form of tag including data about the medicament and how that medicament is made or information relating to the manufacturing and supply of the medicament. It may even be in the form of a "smart card" which enables information not only to be extracted from the tag but also written to the tag. Data and power may be transferred by direct physical contact, or remotely via an RF field.

It is particularly preferred to provide a dispensing system in two parts, one of which can be envisioned as a hand-held hand-actuated dispensing mechanism and the other as a base or docking station into which the hand-held unit may be placed in order to release the latch. Such a docking or base station may be more or less sophisticated and may be self-standing, or alternatively it may operate in cooperation with a remote overall control system, for example a remote computer or computers. In one specific aspect of the present invention, the docking station may contain transmitter/receiver means for communicating with a central control computer enabling exchange of signals/data between the remote computer and the base or docking station and accordingly, if the dispensing device is placed in the base or docking station, between the remote computer and the dispensing device. In such a system, it is entirely possible to arrange by means of suitable programming and suitable easily implemented electronics that the dispensing history of the hand-held device can be uploaded to a central remote computer at the same time or adjacent in time to the remote computer sending the hand-held device appropriate control signals.

The means of communication between a base or docking station and a remote computer can be any appropriate means, for example using cellular telephony techniques, via the Internet or via any other appropriate communications mechanism.

SUMMARY

It is also possible to provide, in the hand-held dispensing device, means for communicating with a separate standard computer device, for example a personal computer, palm-top, PDA or mobile communications device. By including an infra-red or RF communications port in the hand-held device, once communication is established with the docking station and communication is actuated, a dialogue may be established between the patient and a host computer or even with a physician or other adviser. Thus, it is possible, at the same time as dealing with the basic reporting of past use of the device, to enable the patient to fill in a questionnaire, or to enter into the system a query about their condition or a report of current state of health. This "telemedicine" aspect to the dispensing system provides very substantial flexibility of communication between patient and doctor, and enhances clinical care opportunities.

While such a system is extremely beneficial, patient compliance will be patchy such that a patient may end up entering data significantly after the event, when the data may not be as accurate as it would be if it were entered at the correct time. In the worst case, the patient can fail to enter the data entirely.

SUMMARY

WO 01/93801 discloses an apparatus similar to that disclosed in WO 02/32487. The device is provided with input means allowing a user to input certain information on medication consumption. This information is primarily required to allow the unit to compute the desired time at which the medication can be dispensed. The information is stored locally to the device and can be read out later if required and used for research purposes. This goes some way to overcoming the problems with ensuring that the patient enters the data correctly.

According to the first aspect of the present invention, there is provided a dispensing system comprising a dispenser arranged to dispense a quantity of material; a locking mechanism on the dispenser to prevent dispensing of the material; a user interface allowing the user to input data; and a control device remote from the dispenser, the control device arranged to receive the input data and to enable release of the locking mechanism to allow dispensing of the material.

The present invention offers considerable improvement over the system of WO 01/93801. As the control of the locking mechanism is carried out remotely this ensures that the data entered by the patient must be received remotely prior to the dispenser being released to provide a further dosage. This ensures that the data is guaranteed to be received remotely and that it is received in real time. With WO 01/93801, there is no such guarantee as the local device memory is only read out at a later date. Further, as the data is received remotely in real time, it is possible for a medical practitioner to read and interpret the data before allowing a user to take another dosage of the medicament. Such an option is not available in the device of WO 01/93801.

By allowing the patient to communicate in this way, the number of possibilities are opened up. For example, the device can obtain information from the patient in order to make a positive identification of the patient. This may take the form of a number of predetermined questions to which only the authorised individual would know the answers. Alternatively, more sophisticated identification techniques such as fingerprints and retinal scans can be used.

Alternatively, the patient may be faced with a test to determine his/her reaction time allowing the system to determine his/her level of intoxication and regulate the dosage pattern accordingly.

In the case of clinical trials or similar procedures, the system of the invention enables a substantial degree of control and monitoring to be easily and cost-effectively carried out without the ease of use of the medicament for the user or patient being compromised.

Under certain circumstance, it may be advantageous to activate the locking mechanism if the data has not been entered by a fixed time. The system can be arranged such that the locking mechanism can then only be released by the control device.

In its simplest form, the control device may simply detect that information has been received and release the locking mechanism accordingly. However, in a more sophisticated device, the control device may make some qualitative assessment of the input data, for example by determining that all of a desired number of questions have been answered. Alternatively, the control device may include a display to display the input data allowing manual assessment of the data before the locking mechanism is released. As mentioned previously, the system can dispense any material, but is particularly designed for medicament. The medicament may be in the form of tablets, but is preferably in a fluid form which is dispensable in a number of measured doses. The invention is applicable to any type of dispenser with a suitable locking mechanism. However, it is particularly applicable to the device of WO 02/32487.

In the broadest sense, with this device, the dispenser is adapted to receive a sealed or resealable container of material to be dispensed and includes a mechanical actuation mechanism which, when actuated, causes a measured dose of material to be dispensed from the material container, and the actuation mechanism may be inhibited from operation by the locking mechanism.

Preferably, the container and dispenser are provided with means enabling the authenticity of the container placed in the dispenser to be checked.

Preferably, the dispenser is a portable hand-held device.

The system preferably includes a separate base or docking station into or near which the hand-held unit may be placed in order to release the locking mechanism.

The present invention also aims to provide a system having a more flexible means of configuring the dispensing mechanism.

According to a second aspect of the present invention there is provided a dispensing system consisting of a programmable dispensing mechanism adapted to receive a sealed or resealable container containing multiple doses of material to be dispensed, and including a mechanical actuation mechanism which, when actuated, causes a measured dose of material to be dispensed from the material container, and wherein the actuator mechanism may be inhibited from operation by a locking mechanism which, when actuated, locks the device against further dispensing of a dose of material until the release in accordance with a desired dispensing programme; further comprising a cartridge to be received in the dispensing mechanism in place of the container of material to be dispensed, the cartridge containing user specific data, means in the dispensing mechanism to read the data, and control means to control the operation of the dispensing mechanism in accordance with the data.

With this arrangement, the patient can be provided with a cartridge containing patient specific information, such as the type of drugs and the intended dosage regime. This cartridge can be used to configure a dispenser. If the user has a number of dispensers, for example one for use at home, one for use in the car and one for use at work, all of these dispensers can be configured using the cartridge.

Preferably, the cartridge and the dispensing mechanism are provided with means enabling the authenticity of the cartridge placed in the dispensing mechanism to be checked. In this way, the system can be programmed so that only those dispensing mechanisms allocated to a particular user can be configured by the cartridge. The system can also record if a user has attempted to use the cartridge to configure an unauthorised dispensing mechanism.

Preferably, the data in the cartridge can be reprogrammed. This will allow a medical worker to reconfigure a patient's cartridge, for example to change the dosage pattern. Also, a medical worker would be able to change the information on the device to override the date from the cartridge.

Preferably, the data on the cartridge includes a user specific PIN code. If the dispensing mechanism requires a user to input a PIN code for operation, this code can also be included in the cartridge. If the user forgets his code, the cartridge can be inserted into the mechanism to remind the user of the code.

A third aspect of the present invention aims to provide an additional degree of control of the dispensing operation.

According to a third aspect of the present invention there is provided a dispensing system comprising a dispenser arranged to dispense a quantity of material; a locking mechanism on the dispenser to prevent dispensing of the material; a position detector to detect the position of the dispenser; and a control means to activate the locking mechanism to prevent dispensing of the material if the position detector indicates that the dispenser is not within a fixed location.

Thus, the invention allows those prescribing medication to be able to control the location where the medication is taken. For example, the dispensing system can be configured such that it will only dispense medication in a specific clinic or hospital.

In its simplest form, the position detector may be a means to monitor when the dispensing mechanism is beyond a given radius from a fixed point. For example, a docking station may be provided with an RF link to the dispensing mechanism. In this case, the position detector is able to determine the distance between the docking station and the dispensing system and to actuate the locking mechanism if the dispensing mechanism is further than a given distance from the docking station.

For a more sophisticated system the absolute position of the dispensing mechanism may be detected, for example using a global positioning (GPS), cellular positioning (CPS) or triangulation system. This will provide operators with greater flexibility to limit the dispensing of material to certain regions.

As mentioned previously, the system can dispense any material, but is particularly designed for medicament. The medicament may be in the form of tablets, but is preferably in a fluid form which is dispensable in a number of measured doses. The invention is applicable to any type of dispenser with a suitable locking mechanism. However, it is particularly applicable to the device of WO 02/32487.

In the broadest sense, with this device, the dispenser is adapted to receive a sealed or resealable container of material to be dispensed and includes a mechanical, actuation mechanism which, when actuated, causes a measured dose of material to be dispensed from the material container, and the actuation mechanism may be inhibited from operation by the locking mechanism.

Preferably, the container and dispenser are provided with means enabling the authenticity of the container placed in the dispenser to be checked.

Preferably, the dispenser is a portable, hand-held device.

The system preferably includes a separate base or docking station into or near which the hand-held unit must be placed in order to release the locking mechanism.

The three aspects of the invention may be used independently, or together in any combination.

The preferred medicaments for dispensing using the system include unlicensed drugs undergoing clinical trials and controlled drugs such as, drug dependence drugs, for example, narcotics or opiates including cocaine, diamorphine, morphine and the synthetic opioids, amphetamines, flunitrazepam, temazepam, barbiturates, cannabis (or drugs derived therefrom), and lysergide. Indeed any drug defined under the Misuse of drugs Act 1971 as a class A, B or C drug or those defined under the Misuse of drugs regulations 1985 as a schedule 1, 2, 3, 4, or 5 drug would be particularly suited for use with the system of the invention.

BRIEF DESCRIPTION OF THE DRAWINGS

The inventions are illustrated by way of example with reference to the accompanying drawings in which.

DETAILED DESCRIPTION OF THE DRAWINGS

Figure 1:
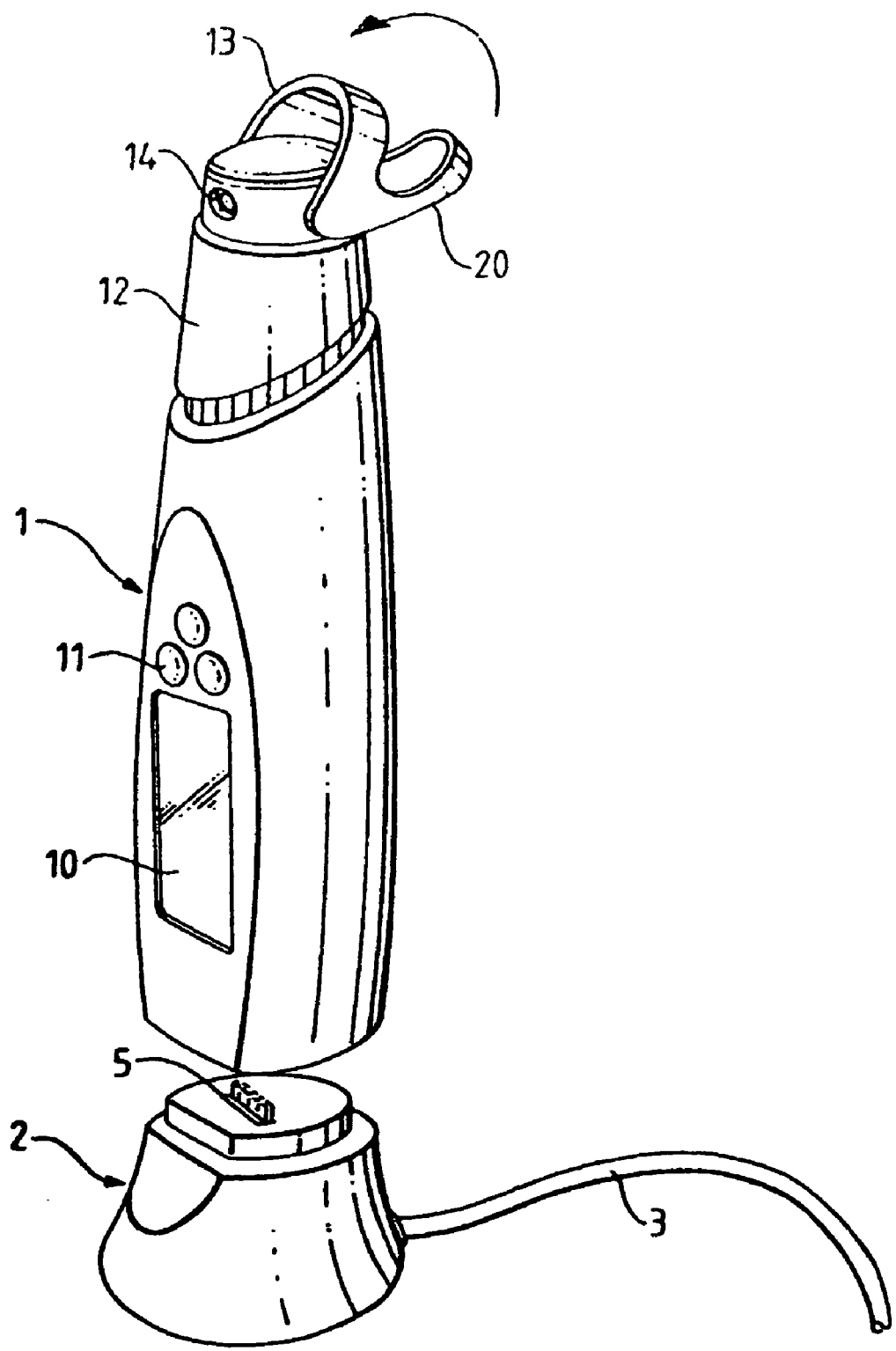
FIG. 1 shows a drug dispensing unit and base station in accordance with the present invention.

Referring to the drawings, FIG. 1 shows a dispensing unit generally denoted 1 which can be placed on top of a base unit generally denoted 2. The base unit is connected via a power and signal cable 3 with appropriate related apparatus, for example to a telephone socket or to a PC interface card. The upper face of the docking station 2 carries a row of connector terminals 5 which can, when the dispensing unit 1 is placed on the docking station, electrically contact corresponding members (not shown in FIGS. 1 and 2) located on the underside of the dispensing unit 1.

The dispensing unit itself is provided with a liquid crystal display screen 10 and some function buttons 11, and has at its upper end a nozzle actuation cap 12 with a lowerable closure tab 13 which can be used to cover an aerosol outlet 14 in cap 12, thus preventing the aerosol outlet being clogged with dust, dirt or other contamination.

Cap 12 may be releasable from the upper end of the main body of the dispensing device as shown in the drawings to enable a canister with a standardised outlet tube to be located within it, the outlet tube being registered with an appropriate aerosol nozzle 14. By pressing the cap 12 down into the main body of dispensing device 1, the aerosol valve may be actuated and a dose of material expelled, whereafter an electromechanical latch within the main body of the dispensing device 1 may act to prevent the cap 12 being pushed into the body of dispensing device 1 a second time until release occurs. Release may occur merely following the passing of a given period of time, but it is highly desirable more positively to control the ability of the device to dispense. For this purpose, it is straightforward to arrange that the latch within the main body of dispensing device 1 will remain locked to prevent a further depression of cap 12 until appropriate steps are taken to release it. For example, release may be effected remotely in accordance with a programmed regime by placing the dispensing unit 1 on to the base station 2 and thereafter having the dispensing station and the base station communicate with one another, whereon, if appropriate, the internal latching may be released. The status of the dispensing device 1 may be shown on screen 10, both before and after placing on the base station. A number of push buttons 11 are provided in order to control input from the user, for example to enable the user to set up a communication link with the remote computer via the base station 2.

Once such a link has been established and e.g. the latch released so that a second dose may be dispensed, the dispensing device 1 may be removed from the base station, held in the hand as shown in FIG. 2, and the cap again depressed in the direction of arrow 30 shown on FIG. 2. It is easy to arrange that when such actuation occurs, the latch within the dispensing unit 1 re-engages to prevent a second dispensing action and separately the status of dispensing unit may change, the change being displayed in window 10.

Alternatively, the device may include suitable control circuitry internally, such circuitry acting to release locking and enable a further dose to be dispensed after a suitable period of time, and preferably including a rewritable memory store to maintain a record of when doses were in fact administered and when and how the device was interacted with by the user. The content of such a store may be automatically transferred to a store in the docking station when the device is docked, or transferred direct to a remote computer if desired.

It is often desirable to record additional information from a patient, for example as to their general state of well being and the effect that the medication has had on them. This can be a useful diagnostic tool for medical practitioners, and is particularly useful in the case of clinical trials. The device therefore includes a means for inputting this information. In its simplest form, this could take the form of a set of questions being displayed on the LCD screen 10 with a set of multiple choice answers which the user selects using function buttons 11. The function buttons 11 could also be used to input text. However, this is likely to be time consuming, and if text input is required, some further device such as lap top computer, PDA, or communications device can be connected to the base station 2 either physically or remotely. Alternatively the communications devices and input devices could have their own link to the remote computer alleviating the need to connect to the base station 2. Alternatively, for patients having difficulty with their manual dexterity, the input device could be a microphone to record the necessary information orally. This can then be converted to text using voice recognition software either locally, or at the remote computer. Alternatively, the text could be typed manually.

In order to ensure patient compliance with the requirements to enter this text, the remote computer is set so as not to release the latch until the information has been recorded, processed and a determination as to what course of action should be taken with respect to the locking or unlocking of the latch has been made from the recorded information and/or the other data from the remote system.

Figure 3:
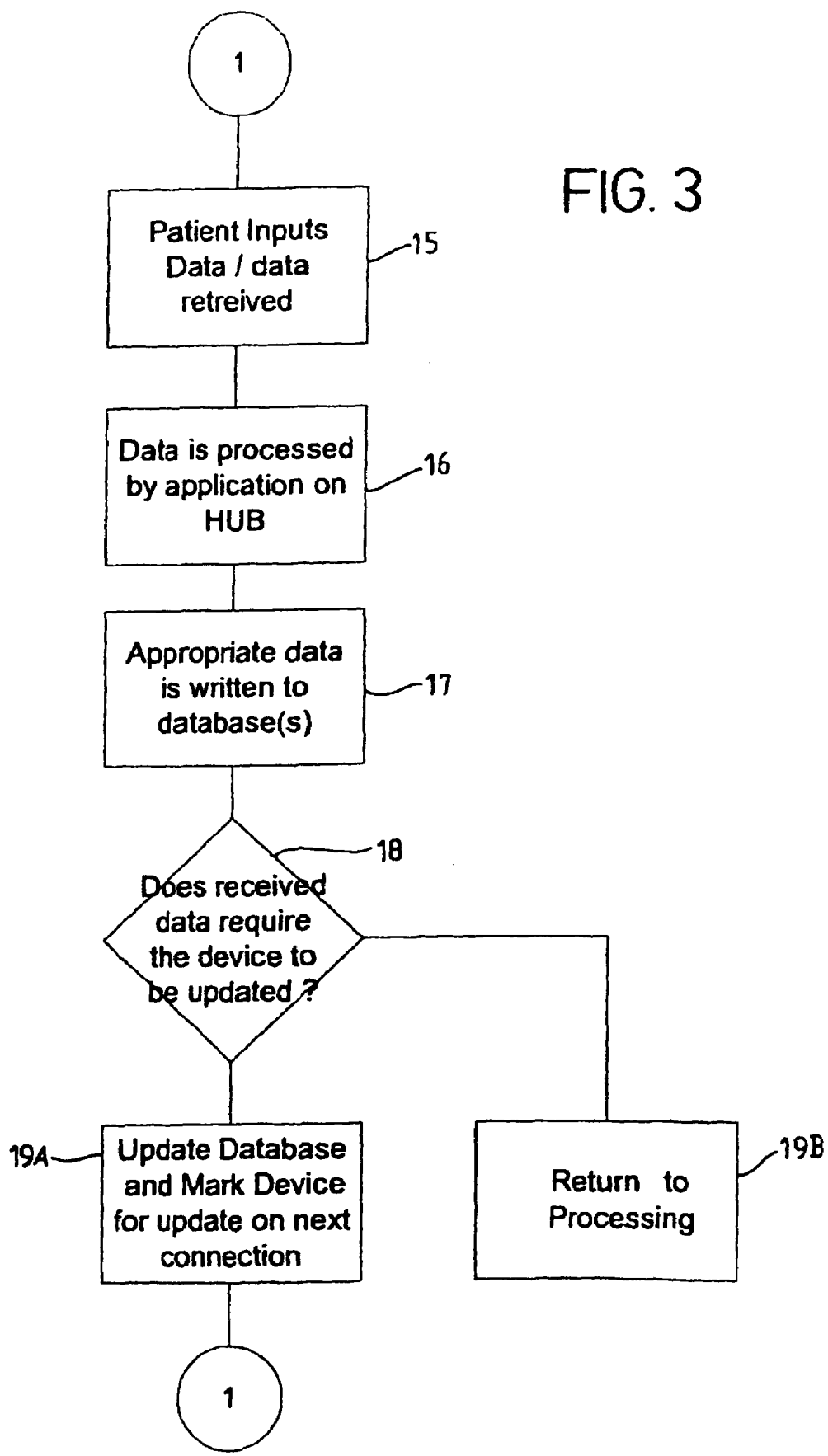
FIG. 3 is a flow diagram of one aspect of the operating system.

FIG. 3 illustrates the operation of this aspect of the invention. The patient inputs data through device 1, or some other device as described above as step 15. This data is transmitted to a remote hub providing a control device where it is processed as step 16 and appropriate data is written to a database at step 17. At step 18, the hub determines whether the received data necessitates any updating of the device. The system has a set of rules that will be used to determine whether or not to update data within the dispenser which will in turn influence the operation of the blocking mechanism. Thus, if the hub determines that the necessary data has been correctly received and derives from the data that the device needs to be updated or the locking mechanism state should be altered, it will update the device at step 19A and will then return to processing at step 19B.

Although this process has been described in relation to additional data input by the user, it is also applicable to information received directly from the device itself relating to the patient usage data. Thus, for example, the hub can be programmed to recognise certain unusual dosage patterns and to alert a medical practitioner, to adjust the dosage regime, or to lock the device to prevent further usage.

If, for example, a patient has a dosage regime of one tablet of a drug three times a day, and the control protocol requires that a patient complete a data entry in an electronic diary before the next dose can be taken, the system will automatically restrict the dose until the diary is completed. An alert can be sent if the dose is not taken or the diary is not completed within a prescribed period. This can give a clinical trial investigator real time information about the dosing/data recording behaviour of the patient group.

The benefit of this device is that the input data is clean at source as it must be entered before the next dose can be dispensed. The system can also be configured to accept data after the drug has been dispersed.

Figure 2:
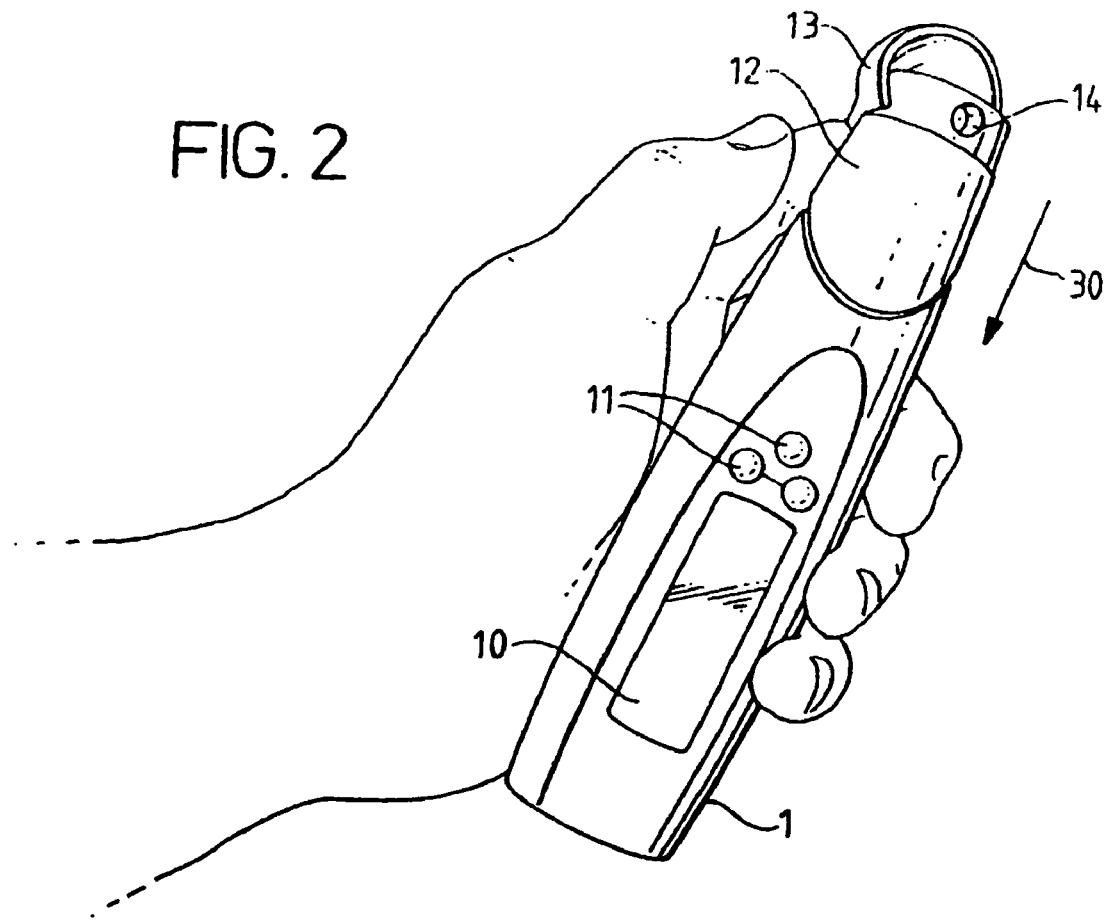
FIG. 2 shows the unit of FIG. 1 about to be used.

As shown in FIG. 1, the closure tab 13 which acts to shield ingress of dirt into the dispensing outlet 14 has an angled out portion 20 which can be engaged by the forefinger of the left hand as shown in FIG. 2 of the drawings in order to achieve dispensing.

Figure 4:
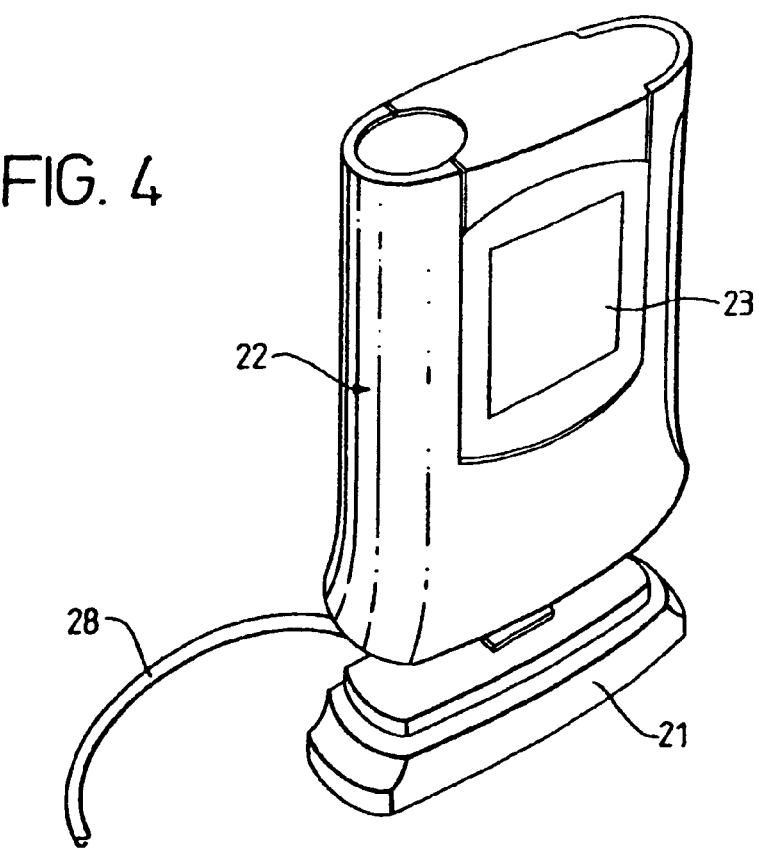
FIG. 4 shows an alternative general view of an alternative dispensing unit and base station.
Figure 5:
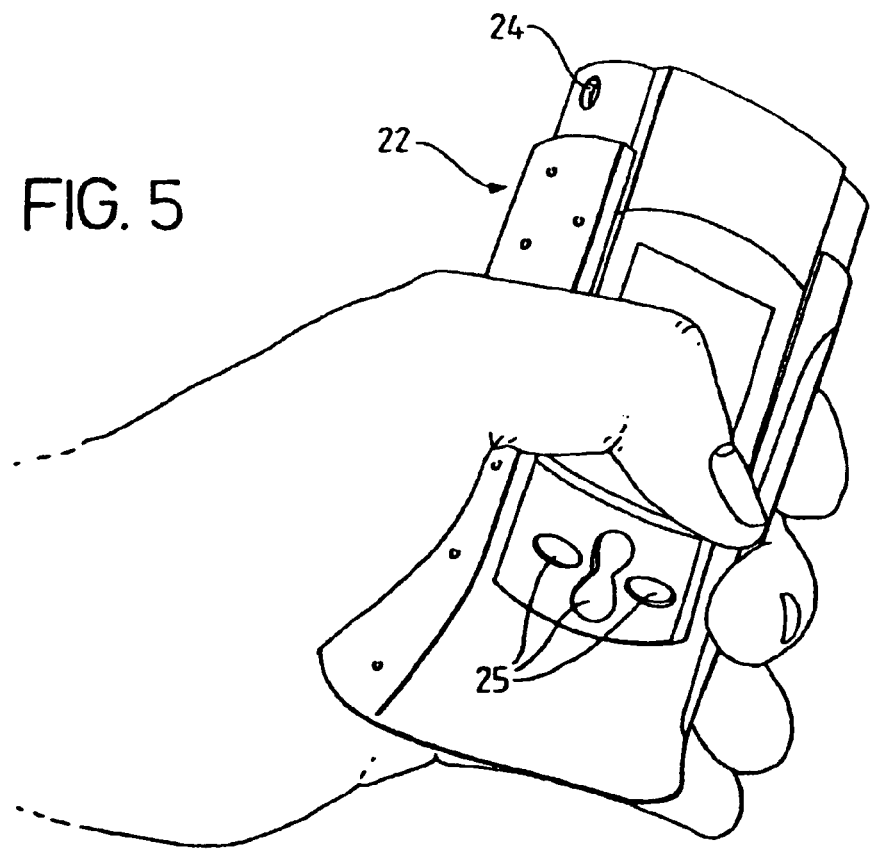
FIG. 5 shows the unit of FIG. 4 in use.

Such an approach is not always desirable, or, indeed, convenient, and it may be particularly awkward for people with arthritis. Accordingly, FIGS. 4 and 5 show an alternative construction where dispensing is achieved by means of a lateral grip across a generally oval cross-section elongate housing which covers the dispensing device. Referring to FIGS. 4 and 5, the system consists again basically of a docking station 21 connected via cable 28 and a squeezable dispensing unit 22. The latter has a display screen 23 in a slidable central section which can be slid up to reveal the nozzle of an aerosol dispensing nozzle 24 which is visible in FIG. 5, but not in FIG. 4. Likewise visible in FIG. 5 but not in FIG. 4 is the set of control buttons 25 which enable the unit to be controlled by the user.

The mechanical construction enabling a squeezing movement exerted as shown in FIG. 5 to be converted into an axial compression to release a dose from a pressurised container via the aerosol nozzle may be simply effected using appropriate standard mechanical constructions, and the mechanical arrangements for latching the device against an immediate second use can likewise be simply and appropriately constructed. Located within the housings of the respective dispensing devices 1 and 22 shown in FIGS. 1 and 4 respectively are also appropriate electronics and a power supply or back-up power supply, for example one or more battery cells. If desired, the electronics may be rechargeable and recharging can take place when the respective dispensing unit is located on its docking station 2 or 21. This can obviously be effected automatically by appropriate design and programming.

Figure 6A:
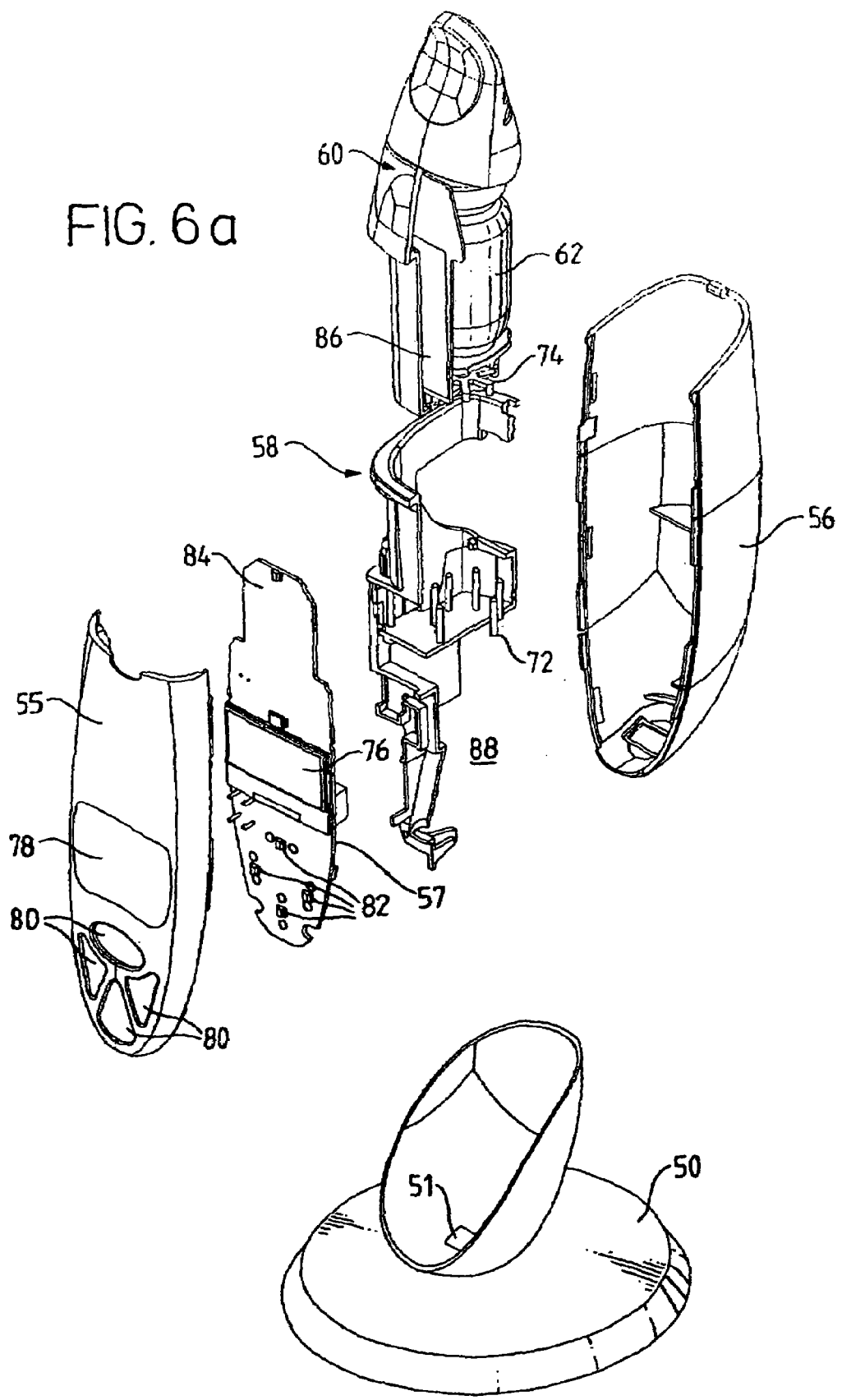
FIGS. 6a and 6b show in exploded view from front and back respectively a third embodiment of a drug-dispensing unit and base station in accordance with the invention.
Figure 6B:
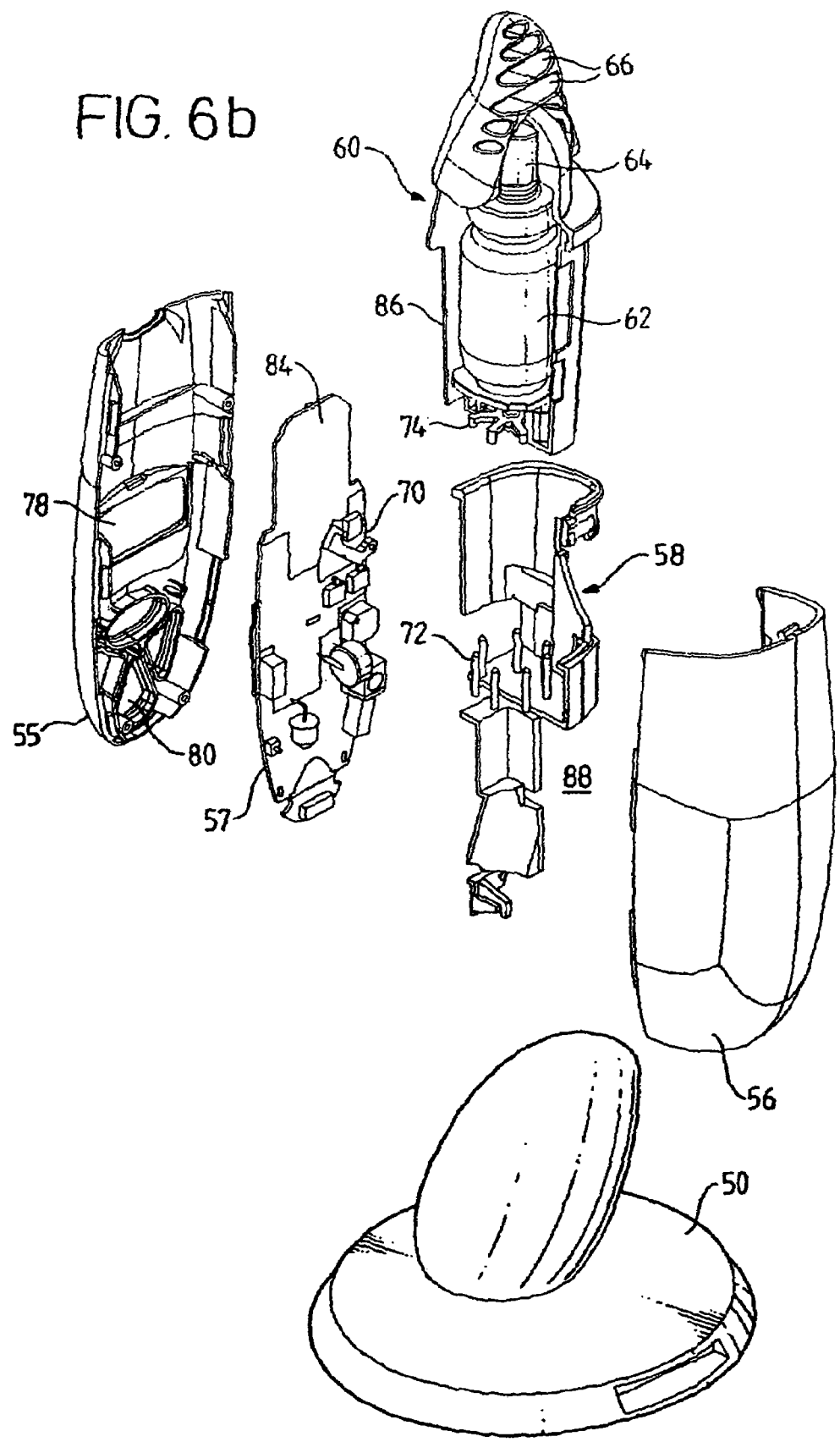

FIGS. 6a and 6b show a further embodiment of the dispensing system, in each case in exploded view from front and back respectively. Referring to these figures, from which detail has been omitted for the sake of clarity, the system consists of a base station 50 into which a hand-held dispenser can be set when needed. A contact pad 51 enables signals to be sent to and from the hand-held unit when it is placed in base station 50.

The hand-held unit consists basically of front and rear casing shells 55, 56 respectively which clip together round a circuit board 57 and an internal moulded receptacle unit 58. Shown above unit 58 in the drawing is a removable cartridge housing 60 which may be locked into place in the assembled housing or released therefrom as and when necessary. Cartridge housing 60 is designed to receive a container of medicament 62, here in the form of an aerosol spray canister with a dispensing nozzle 64 which lies in the upper part of housing 60 having a number of weight reducing indentations 66, and which is suitably configured to enable a dose of medicament to be dispensed sub-lingually via apertures (not shown).

Circuit board 57 bears a latch assembly 70 designed to interact with portions of housing 60 to enable the housing to be latched in place or removed upwardly from the rest of the device. The latching assembly also allows, at appropriate intervals controlled by programming, the housing 60 to be pushed down in the upper half of moulding 58 to enable a set of pins 72 to press on the ends of the arms of a spider 74 and so cause the container 62 to be pressed towards the nozzle 64, so dispensing a dose of medicament therefrom. After one (or if programmed appropriately more) such compressions, the latch assembly may lock the housing 60 against further such movement until released when the next dose of medicament is due to be dispensed. The exact nature of the operation of the spider 74 and associated components is described in more detail in our copending application filed on even date and claiming the priority of GB patent application 0025811.1

Circuit board 57 carries a display screen 76 visible through a window 78 in casing front 55. In use of the device, this screen can carry a message to the user, for example indicating the state of the device, ready to dispense or locked. Casing front 55 also has four apertures 80 which, when the device is assembled, are filled with rubbery press buttons (not shown in the drawing), which enable actuation of four switches 82 set in circuit board 57. The upper end 84 of board 57 carries a printed RF antenna which enables the checking of a so-called RF tag 86 which forms part of the cartridge assembly. This enables the system to check just what medicament has been loaded into it when a fresh container 62 and associated tag 86 are inserted into the upper housing 60 and that housing latched into position in moulding 58.

The hand-held unit may be powered by a suitable battery which can fit in the area denoted 88 in the drawing.

It will be readily appreciated that using devices as shown in FIGS. 1, 5 and 6a/6b, the degree of control of dosage can be very high and the ease of recording and monitoring of the dosage regime is substantial. If, for example, the base station 2, 21 or 50 is connected into the normal telephone system, a central controlling computer can monitor the operation of the device by the user remotely, and any anomalous or undesired administration can be detected rapidly and appropriate immediate action taken. A further advantage is that, for example, a sounder is easily incorporated into the base unit which can be programmed by the central computer to emit an audible signal, e.g. to remind a user that dosage is overdue. The operating rules may provide that if within say 5 minutes of the emission of such an audible signal the user does not acknowledge having heard it, an appropriate record can be made of this event.

As noted above, the device may itself include appropriate control circuitry including a memory device. In such a case, it is possible to programme that circuitry (and a remote computer) so that when the device is first docked, it starts by establishing a communication link with the remote computer, which can then initially set-up the device with appropriate parameters for a patient. These could, for example, govern the length of a PIN No required to access the docking station and details of the proposed dosage regime, for example initially loading an expected running average based on the prior doctor/patient experience. This false average could form the foundation for a continuing running average that is calculated with time and use. This data would constitute a benchmark, enabling the device thereafter to monitor usage levels and to detect any incidence of deviation. The time and frequency of use, and other events such as opening of the casing or tampering with it, may be stored and uploaded to a central system as desired. The system may be programmed to issue restrictive orders on the patient's medication, or it may simply be programmed to report data, so as to highlight areas of concern and alert the appropriate GP or specialist for attention at the patient's next appointment.

As noted above with reference to FIGS. 6a/6b, in place of or supplementary to the downloading of data via a remote link, data may be stored with the container for the material to be dispensed. In some areas, there is already a requirement for a form of tagging on medicinal canisters that can be read or written to. This tag carries information as to the medication type, use-by dates, etc. and when used with a device according to the present invention, the tag may be accessed by the device (and/or via the docking station), and the device could be programmed to write to the tag the number of doses left in case of removal from the device. The tag could have a large memory capacity free for other uses. On return of the canister to the pharmacist, the usage data written to the canister can then be interrogated. Data as to when the canister was used and by whom, would remain with the canister of medication that was dispensed. This method of data management may prove to be more convenient and effective in some cases than online monitoring with the device (including the canister) being mated with the docking station.

The device may be used to dispense medication at fixed times throughout the day. Alternatively, it can be programmed in a "free dosing" mode. This caters for the situation where a daily maximum dosage must be adhered to, but a specific time when the medication should be taken cannot be predefined, for example in the case of an analgesic type drug. The device itself, or the medicinal cannister can be programmed to set the free dosing mode, i.e. to allow the user to dose freely during a predefined period until a maximum allowable number of doses is reached.

In certain circumstances, it may be desirable to programme the medicinal cannister to a free dosing mode, but to allow the device to override this mode, thereby allowing, for example, the free dosing mode to be manually overridden by a doctor from a remote location. The device or medicinal cannister can be programmed with different dispensing regimes for different days of the week, thereby varying the daily dosage.

It can be seen that a wide variety of modifications may be made to the overall general construction and design described above, many of them easily made simply by changing computer programmes. Such changes could be made "online" when the hand-held unit is in the docking or base station and in communication with a host computer. The system is of particular value in the monitoring and analysis of administration during a controlled trial, enabling it to be highly automated and reliable. In particular, detection of activity outside the instructions or constraints of the trial can be immediately and automatically achieved.

Figure 7:
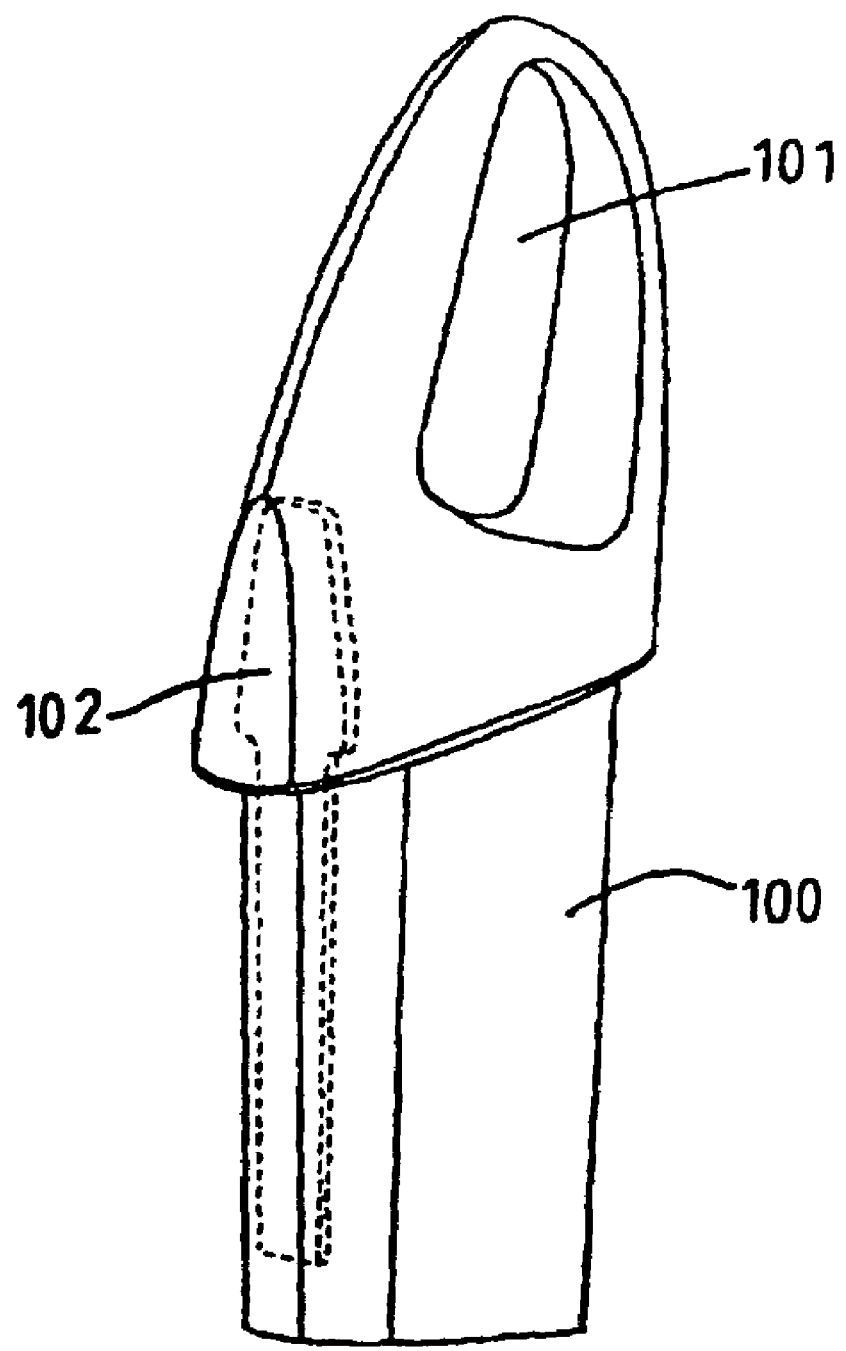
FIG. 7 is a perspective view of a cartridge for insertion into the dispenser previously described.

In addition to or instead of configuring the device remotely from the computer via a communication link, an alternative means configuration will now be described with reference to FIG. 7. This discloses a cartridge 100 designed to fit in a dispenser of FIGS. 6a and 6b. Similar arrangements using appropriately shaped cartridges may be employed with the examples of the previous figures. The lower half of the cartridge 100 is shaped in the same way as the housing 60 so as to fit into the same socket in the dispenser. The upper part of the cartridge 100 may be shaped in any way, and in this case has an aperture 101 for ease of removal. The cartridge 100 contains no medication, but has a RF tag 102 sized and positioned similarly to RF tag 86. This tag 102 contains the patient specific information used to configure the device.

If the cartridge 100 is configured for a particular device and is subsequently inserted into that device, only that device will be configured. If however the same cartridge is inserted into another device that the cartridge has not been configured for the cartridge will not authorise that dispense device. It will however cause the device that it was inserted into to log the serial number of the cartridge in its memory. When the unauthorised dispense device is next downloaded it will become apparent that the cartridge has been inserted into the device.

If however a user has a number of dispense devices, say one in the home another in the car and a further device in the office, the cartridge 100 could be configured to authenticate and configure all devices upon insertion of the cartridge into the relevant device.

When patients use the device they will have to enter their secure PIN code to access the drugs. On occasions the patient may forget the PIN code. In this event the user can insert the cartridge into the device which will replay the PIN by way of flashing the appropriate buttons and prompting the user to confirm by way of pressing the button indicated.

In order to provide the ability to prevent the dispenser from dispensing when it is not an authorised location, a number of approaches may be adopted.

Most simply, the dispensing unit 1 and base unit 2 of the example of FIG. 1 may be provided with an RF transmission mechanism. Signals received by the base unit 2 from the dispenser 1 are analysed by the control circuitry to determine whether or not the dispensing unit 1 is within an authorised radius of the docking station. If so, the control circuitry will release the locking mechanism. If not, the locking mechanism will remain in place. Similar considerations apply to the example of FIGS. 6a and 6b, where distance from the base station 50 can be monitored.

The dispensing at an authorised location may be used in combination with other pre-programmed parameters referred to above, such as dosage patterns etc. A user will therefore only be able to access the drugs when at an authorised location and when it is time to dispense the dose in accordance with the other pre-programmed parameters.

Alternatively, the location of a dispenser may be monitored using global positioning (GPS), cellular positioning (CPS) or a triangulation system.

The invention claimed is:

1. A dispensing system comprising
a dispenser arranged to dispense a quantity of material when the dispenser is present in an authorized location;
a locking mechanism on the dispenser to prevent dispensing of the material;
a position detector to detect whether the dispenser is present in the authorized location; and
a controller to activate the locking mechanism to prevent dispensing of the material if the position detector indicates that the dispenser is not within the authorized location.

2. A system according to claim 1, wherein the position detector monitors when the dispensing mechanism is beyond a given radius within the authorized location.

3. A system according to claim 1, wherein the position detector monitors the absolute position of the dispenser to detect whether the dispenser is present in the authorized location.

4. A system according to claim 1, wherein the dispenser is adapted to receive a sealed or resealable container of material to be dispensed and includes a mechanical actuation mechanism which, when actuated, causes a measured dose of material to be dispensed from the material container, and the actuation mechanism may be inhibited from operation by the locking mechanism.

5. A system according to claim 4, wherein the container and dispenser are provided with means enabling the authenticity of the container placed in the dispenser to be checked.

6. A system according to claim 1, wherein the dispenser is a portable, hand-held device.

7. A system according to claim 6, further comprising a separate base or docking station into or near which the hand-held device must be placed in order to release the locking mechanism.

8. A dispensing system comprising
a dispenser arranged to dispense a quantity of material;
a locking mechanism on the dispenser to prevent dispensing of the material;
a position detector to detect the position of the dispenser;

a control means to activate the locking mechanism to prevent dispensing of the material if the position detector indicates that the dispenser is not within a fixed location; and a separate base or docking station into or near which the dispenser must be placed in order to release the locking mechanism;

wherein the dispenser is adapted to receive a sealed or resealable container of material to be dispensed and includes a mechanical actuation mechanism which, when actuated, causes a measured dose of material to be dispensed from the material container, and the actuation mechanism may be inhibited from operation by the locking mechanism, and wherein the container and dispenser include means enabling the authenticity of the container placed in the dispenser to be checked.

9. A system according to claim 8, wherein the position detector is a means to monitor when the dispensing mechanism is beyond a given radius from a fixed point.

10. A system according to claim 8, wherein the position detector is a means to monitor the absolute position of the dispenser.

11. A system according to claim 8, wherein the dispenser is a portable, hand-held device.

* * * * *